United States Patent [19]

Hashimoto et al.

[11] 4,332,896

[45] Jun. 1, 1982

[54] PROCESS FOR PRODUCING CEPHALOSPORIN ANALOGS

[75] Inventors: Yukio Hashimoto, Yamato; Kazuo Kimura, Hofu; Tadashi Hirata, Yokohama; Takehiro Ogasa; Shigeru Kobayashi, both of Machida; Ikuo Matsukuma, Yokkaichi, all of Japan

[73] Assignee: Kyowa Hakko Kogyo Co., Ltd., Tokyo, Japan

[21] Appl. No.: 140,184

[22] Filed: Apr. 14, 1980

[30] Foreign Application Priority Data

Apr. 14, 1979 [JP] Japan ................................. 54-45897
Nov. 1, 1979 [JP] Japan ............................... 54-140476

[51] Int. Cl.$^3$ ........................................... C12P 17/18
[52] U.S. Cl. ..................................... 435/119; 546/112
[58] Field of Search ................................. 435/50, 119

[56] References Cited

U.S. PATENT DOCUMENTS 3,816,253  6/1974  Takahashi et al. ................. 435/50
3,945,888  3/1976  Takohashi et al. ................. 435/50

OTHER PUBLICATIONS

J. Am. Chem. Soc. vol. 96, pp. 7584+7585 (1974).

Primary Examiner—Alvin E. Tanenholtz
Attorney, Agent, or Firm—Fitzpatrick, Cella, Harper & Scinto

[57] ABSTRACT

Optically active cephalosporin analogs are produced by an optically selective acylation reaction. The reaction is carried out in the presence of a microbial enzyme which catalyzes the selective optical acylation. The products thus obtained are useful as antibacterial agents.

5 Claims, No Drawings

PROCESS FOR PRODUCING CEPHALOSPORIN ANALOGS

BACKGROUND OF THE INVENTION

The present invention relates to a process for producing optically active cephalosporin analogs represented by the formula

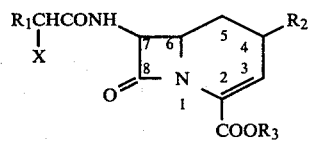

wherein $R_1$ represents a substituted or unsubstituted saturated or unsaturated six-membered carbocyclic or five-membered heterocyclic group, $R_2$ represents a hydrogen or a lower alkyl group, $R_3$ represents a hydrogen or a protective group of carboxylic acid, the hydrogens at the 6- and 7-positions have cis configuration and X represents a hydrogen, a lower alkyl group, a hydroxy group, a carboxy group or an amino group and salts thereof.

A carbacephem compound, which is named according to the nomenclature in J. Am. Chem. Soc. 96, 7582 (1974), wherein the sulfur atom of cephalosporin is substituted with a carbon atom and which has a substituted methyl group at the 3-position is described in the above reference and J. Med. Chem. 20, 551 (1977).

Heretofore, the present inventors have succeeded in preparing carbacephem compounds having various substituents at the 4-, 5- and 3-positions. The compounds are described in the specifications of Japanese Patent Application Nos. 34696/78, (Japanese Published Unexamined Patent Application No. 128591/79), 122403/78, 133072/78, 162005/78 and 8408/79, U.S. patent application Ser. No. 23,645 (hereinafter "U.S. Ser. No. 23,645") filed Mar. 23, 1979 now U.S. Pat. No. 4,291,164 and German Offenlegungsschrift No. 2911786 (hereinafter "G.O. No. 2911786").

Furthermore, the present inventors have succeeded in preparing novel acylated carbacephems which are new antibiotics having strong antibacterial activity. The compounds are described in Japanese Patent Application Nos. 34696/78, 122402/78, 127027/78, 133071/78, 162006/78, 162007/78 and 8409/79, U.S. patent application Ser. No. 23,646 filed Mar. 23, 1979 (hereinafter "U.S. Ser. No. 23,646") and German Offenlegungsschrift No. 2911787 (hereinafter "G.O. No. 2911787").

As is described in the above-mentioned specifications, the cephalosporin analogs are prepared by synthetic methods using optically inactive starting compounds, and the final products are essentially optically inactive dl [represented by (±)] compounds.

That is, compounds represented by the formula (III)

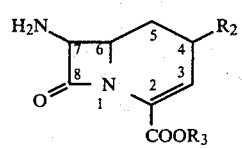

wherein $R_3$ has the same significance as defined above, $R_2$ represents a hydrogen or a lower alkyl group and the hydrogen atoms at the 6- and 7-positions have cis configuration are present as a mixture of equal amounts of the mirror image compounds represented by the formulae (III-1) and (III-2)

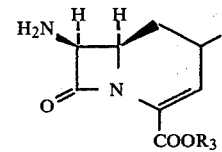 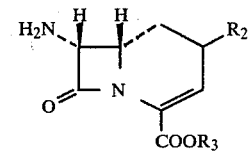

(III-1)  (III-2)

As a result, the acyl compounds derived from such carbacephem compounds are also optically inactive.

On the other hand, it is known that an optically active acyl group, such as a D-phenylglycyl group, can be introduced to an optically inactive carbacephem compound, for example, a compound represented by the formula (IV)

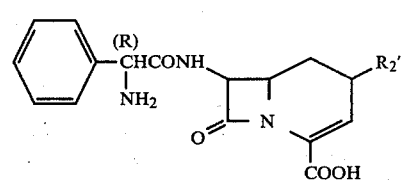

wherein $R_2'$ represents a hydrogen or a methyl group and thereafter separated to diastereoisomers as is described in a Reference Example hereinafter and Japanese Patent Application No. 127027/78. However, this method is complicated because in the preparation of Compound (IV) protection and elimination processes of the amino group or carboxyl group are required.

In Japanese Patent Application No. 14533/79 and U.S. patent application Ser. No. 119451, filed Feb. 7, 1980, of the present inventors, optically active carbacephem compounds are prepared by microbial enzymatic action. This method is, however, also complicated in that it requires a reaction to introduce an acyl group to an optically active carbacephem compound obtained separately in order to obtain an acyl derivative having an optically active carbacephem ring.

There have been reports of the enzymatic acylation of naturally occurring β-lactam compounds such as 6-aminopenicillanic acid which is the ring of penicillins, 7-aminocephalosporanic acid and 7-aminodeacetoxycephalosporanic acid which are the ring of cephalosporins. However, there have been no reports of successful enzymatic acylation of a β-lactam compound synthetically prepared having a carbacephem ring.

Therefore, a need exists for a direct process by which optically active synthetic carbacephems can be prepared. To this end, it has now been found that optically active acyl derivatives having a carbacephem ring can be directly prepared by an enzymatic reaction using microorganisms. The fact that such microorganisms have an ability for acylating with absolute optical selectivity a carbacephem compound synthetically prepared is a novel finding.

SUMMARY OF THE INVENTION

In accordance with the present invention, optically active cephalosporin analogs represented by the formula (I)

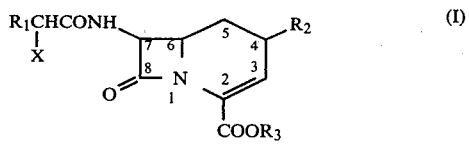

wherein $R_1$ represents a substituted or unsubstituted saturated or unsaturated six-membered carbocyclic or five-membered heterocyclic group, $R_2$ represents a hydrogen or a lower alkyl group, $R_3$ represents a hydrogen or a protective group of carboxylic acid, X represents a hydrogen, a lower alkyl group, a hydroxy group, a carboxy group or an amino group, and the hydrogens at the 6- and 7-positions have cis configuration and salts thereof are produced by reacting an α, α-disubstituted carboxylic acid represented by the formula (II)

wherein $R_1$ and X have the same significance as defined above or a reactive derivative thereof with a compound represented by the formula (III) or (III-1)

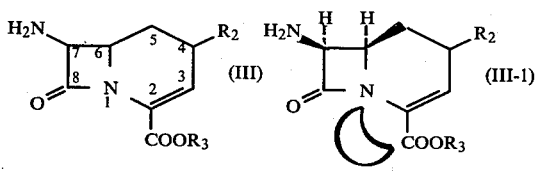

wherein $R_2$ and $R_3$ have the same significance as defined above in the presence of a microorganism having the ability of producing optically active compounds of the cephalosporin analogs represented by the general formula (I) from the α, α-disubstituted carboxylic acid or reactive derivative thereof and the compound represented by the formula (III), or (III-1) and belonging to the genus Pseudomonas, Xanthomonas, Escherichia, Aeromonas, Achromobacter, Arthrobacter, Acetobacter, Alcaligenes, Kluyvera, Gluconobacter, Clostridium, Comamonas, Corynebacterium, Sarcina, Staphylococcus, Spirillum, Bacillus, Flavobacterium, Brevibacterium, Protaminobacter, Beneckea, Micrococcus, Proteus, Mycoplana or Rhodopseudomonas, a culture broth of the microorganism, a treated matter of the culture broth or an enzyme produced by the microorganism.

The acyl derivatives having an optically active carbacephem ring obtained in the present invention are assumed to have the absolute (6R, 7S) structure represented by the formula [I-1]

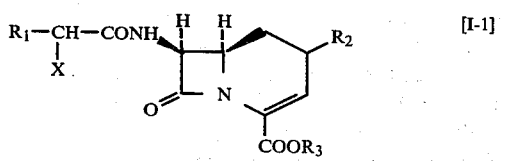

from strong antimicrobial activity compared with the corresponding optically inactive acyl derivative and the relationship between the absolute structure of cephalosporins and activities thereof.

In the description which follows, the compounds are named according to the assumed absolute structure. Moreover, in the following description, the compounds represented by the general formula (I), (II), etc. are sometimes referred to as Compound (I), Compound (II) etc., respectively.

DESCRIPTION OF THE INVENTION

According to the present invention, when an α, α-disubstituted carboxylic acid represented by the formula (II)

wherein $R_1$ and X have the same significance as defined above or a reactive derivative thereof and Compound (III) are reacted in the presence of a culture broth of a microorganism belonging to the genus Aeromonas, Achromobacter, Arthrobacter, Acetobacter, Alcaligenes, Escherichia, Xanthomonas, Kluyvera, Gluconobacter, Clostridium, Comamonas, Corynebacterium, Sarcina, Staphylococcus, Spirillum, Bacillus, Pseudomonas, Flavobacterium, Brevibacterium, Protaminobacter, Proteus, Beneckea, Micrococcus, Mycoplana or Rhodopseudomonas, a treated portion thereof or an enzyme extracted therefrom, only one mirror image compound i.e., Compound (III-1) is acylated selectively with Compound (II).

The present invention thus provides a method for producing Compound (I-1) using a microorganism having an ability of producing Compound (I-1) from Compound (III-1) or dl-Compound (III) and Compound (II).

Compound (III) used in the present invention and a method for the production thereof are described in Japanese Published Unexamined patent application No. 128591/79, U.S. patent application Ser. No. 23,645 filed Mar. 23, 1979 and G.O. No. 2911786. Compound (III-1) is produced according to the method described in Japanese patent application No. 14533/79 and U.S. patent application Ser. No. 119,451 filed Feb. 7, 1980. For ease of reference, a suitable method of producing Compound (III-1) is also described in a Reference Example below.

As the saturated or unsaturated six-membered carbocyclic and five-membered heterocyclic group defined by the variable $R_1$, a phenyl group, cyclohexyl group, cyclohexenyl group, cyclohexadienyl group, thienyl group and furyl group are exemplified. As the substituent, an hydroxy group, halogens, nitro group, amino group, methansulfonamide group, and the like are appropriate. As alkyl group for $R_2$, a straight-chain or branched lower alkyl group such as methyl group, ethyl group, n-propyl group, i-propyl group, n-butyl group, i-butyl group, sec-butyl group, t-butyl group, and the like are suitable. As alkyl group for X, a straight-chain or branched alkyl groups having 1 to 5 carbon atoms such as methyl group, ethyl group, n-propyl group, i-propyl group, n-butyl group, i-butyl group, sec-butyl group, t-butyl group and the like are suitable.

As used herein, the term reactive derivative of Compound (II), means a compound which yields Compound (II) by hydrolysis with a microorganism used in the present invention, including the culture broth of the microorganism, a treated portion of the culture broth and/or an enzyme produced by the microorganism; and typical of such compounds are an alkylester with a methyl group, ethyl group, and the like, and a thioethylester with thiogylycollic acid.

As the $R_3$ group, the following are suitable:

a straight-chain or branched alkyl group having 1 to 5 carbon atoms such as methyl group, ethyl group, n-propyl group, i-propyl group, n-butyl group, i-butyl group, sec-butyl group, t-butyl group, and the like;

a straight-chain or branched alkoxymethyl group having 1 to 5 carbon atoms such as methoxymethyl group, ethoxymethyl group, and the like;

a straight-chain or branched halogenated alkyl group having 1 to 5 carbon atoms such as chloromethyl group, 2,2,2-trichloroethyl group, 2,2,2-trifluoroethyl group, and the like;

a lower alkylsulfonylethyl group such as methylsulfonylethyl group, ethylsulfonylethyl group, and the like;

a arylmethyl group having 7 to 12 carbon atoms such as benzyl group, diphenylmethyl group, trityl group, triphenylmethyl group, and the like;

a substituted arylmethyl group having 7 to 20 carbon atoms wherein the substituent is methoxy group, nitro group, or the like and the number of the substituents on the phenyl ring is 1 to 5; and a protective group of carboxylic acid represented by the formula (V)

wherein $R_4$ represents a straight-chain or branched lower alkyl group having 1 to 5 carbon atoms, a straight-chain or branched lower alkoxy group having 1 to 5 carbon atoms, or a phenyl group, and $R_5$ represents a hydrogen or a straight-chain or branched lower alkyl group having 1 to 5 carbon atoms.

The optically selective acylation reaction of Compound (II) and Compound (III) and the acylation reaction of Compound (II) and Compound (III-1) are carried out by using a microorganism having the ability of producing optically active Compound (I) or Compound (I-1) from Compound (II) and Compound (III), or Compound (II) and Compound (III-1) by acylation reaction, a culture broth of the microorganism, a treated portion of the culture broth and/or an enzyme produced therefrom. Suitable such microorganisms are disclosed in copending U.S. patent application Ser. No. 119,451, filed Feb. 7, 1980 and belong to the genus Aeromonas, Achromobacter, Arthrobacter, Acetobacter, Alcaligenes, Escherichia, Xanthomonas, Kluyvera, Gluconobacter, Clostridium, Comamonas, Corynebacterium, Sarcina, Staphylococcus, Spirillum, Bacillus, Pseudomonas, Flavobacterium, Brevibacterium, Protaminobacter, Proteus, Beneckea, Micrococcus, Mycoplana or Rhodopseudomonas. The following strains are preferred examples of the microorganisms suitable for the present invention.

| | |
|---|---|
| Aeromonas hydrophila | IFO 12634 |
| Achromobacter aceris | IFO 3320 |
| Arthrobacter simplex | ATCC 15799 |
| Acetobacter aurantius | IFO 3245 |
| Acetobacter sp. | ATCC 21760 |
| Alcaligenes faecalis | ATCC 8750 |
| Escherichia coli | ATCC 11105 |
| Escherichia coli | ATCC 13281 |
| Xanthomonas citri | IFO 3835 |
| Xanthomonas physalidicola | IFO 13555 |
| Kluyvera citrophila | ATCC 21285 |
| Gluconobacter liquefaciens | ATCC 14835 |
| Gluconobater dioxyacetonicus | IFO 3271 |
| Clostridium acetobutylicum | ATCC 824 |
| Comamonas terrigena | IFO 12685 |
| Corynebacterium tritici | IFO 12164 |
| Sarcina lutea | ATCC 9341 |
| Staphylococcus aureus | IFO 3060 |
| Spirillum metamorphum | IFO 12012 |
| Bacillus megaterium | ATCC 14945 |
| Pseudomonas melanogenum | ATCC 17808 |
| Pseudomonas aeruginosa | IFO 3451 |
| Flavobacterium sp. | ATCC 21429 |
| Brevibacterium cerinum | ATCC 15112 |
| Protaminobacter alboflavus | IFO 13221 |
| Proteus rettgeri | ATCC 9250 |
| Beneckea hyperoptica | ATCC 15803 |
| Micrococcus luteus | AHU 1427 |
| Mycoplana bullata | IFO 13267 |
| Mycoplana dimorpha | IFO 13213 |
| Rhodopseudomonas spheroides | ATCC 21286 |

For the optically selective acylation reaction, the following substances may be used.

1. The culture liquor of the microorganism or a treated portion thereof.
2. Cell bodies recovered from the culture broth by centrifugation which may be washed with saline water (usually about 1%), buffer solution and the like, or a cell suspension.
3. A disrupted cell suspension, i.e., a suspension of the cell bodies disrupted mechanically or chemically.
4. A cell free extract, i.e., a liquid obtained by removing the disrupted cell bodies from the disrupted cell suspension.
5. A purified enzyme solution which is obtained by recovering the enzyme protein with ammonium sulfate from the cell free extract and subjecting the enzyme protein to gel filtration, ion-exchange cellulose column chromatography, ion-exchange sephadex column chromatography, and the like.

Cells or the purified enzyme immobilized by a conventional method may also be used.

The reaction is generally carried out at a temperature of from 0° to 50° C., preferably 15° to 35° C. and at a pH of 5 to 8 in an inactive solvent which does not affect the reaction.

As the solvent for the reaction, water is most preferably used. Organic solvents such as acetone, methanol, ethanol, N,N-dimethylformamide, dimethylsulfoxide, and the like may be used alone or in combination with water. It is also effective to add phosphate buffer, Veronal buffer or citric acid buffer to control the pH in the reaction. The reaction time varies according to the particular enzyme used and concentration thereof as well as the substrate and concentration thereof, reaction temperature or reaction pH. However, the reaction time is generally 30 minutes to 24 hours. It is most preferable to terminate the reaction when the reaction ratio reaches maximum.

The concentration of microbial cells is preferably 1 to 50 mg by dry weight per 1 ml of the reaction solution. When a purified enzyme is used, it is appropriate to use an amount of enzyme having the same activity as that of the dry cells. The substrate Compound (II) is used in an amount of 0.5 to 50 mg per 1 ml of the reaction solution.

Compound (III) is used in an amount of 0.1 to 50 mg per 1 ml of the reaction solution.

In the event the microorganism utilized also produces an enzyme such as $\beta$-lactamase, esterase or the like, which tends to prevent the desired reaction, such microorganisms can be mutated by known techniques to obtain a mutant strain which has a reduced productivity of the undesirable enzyme. Alternatively, inhibitors of such enzymes may be added in the reaction system to raise the reaction ratio.

After the completion of the reaction, isolation of the desired compound is carried out by conventional methods employed in the isolation and purification of organic compounds from culture liquors such as absorption using various carriers, ion-exchange chromatography, gel filtration, liquid-liquid extraction, and the like.

Certain specific embodiments of the invention are illustrated by the following representative examples.

EXAMPLE 1

Preparation of (+)-7-[(R)-2-phenyl-2-aminoacetamido]-1-azabicyclo[4,2,0]oct-2-en-8-on-2-carboxylic acid [referred to as Compound (A) hereinafter]:

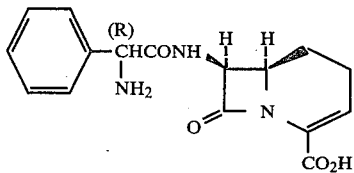

Cultivation of a microorganism having an ability of optically selective acylation As a seed strain, *Pseudomonas melanogenum* ATCC 17808, the biological properties of which are described in the Journal of the Agricultural Chemical Society of Japan, 37, 71(1963) is used.

As the seed medium, an aqueous solution containing 1% polypeptone, 1% yeast extract, 0.5% meat extract, 0.5% sodium glutamate and 0.25% sodium chloride and adjusted at a pH of 7.0 with 5 N-NaOH is used. One loopful of the seed strain is inoculated into 10 ml of the seed medium in a 50 ml large test tube and culturing is carried out at a temperature of 30° C. for 24 hours. The entire amount of the seed medium is then put into 300 ml of a culture medium of the same composition as the seed medium in a 2 L. Erlenmeyer flask and culturing is carried out with shaking at a temperature of 30° C.

Preparation of disrupted cell suspension

After culturing for 24 hours, the cell bodies are recovered from the culture broth by centrifugation and washed twice with 50 ml of 0.9% saline solution. The cells are then suspended in a concentration of 40 mg/ml by dry weight in 1/30 M phosphate buffer. Then, 10 ml of the cell suspension is put into a 50 ml large test tube and subjected to ultrasonic disintegration at 200 W for 2 minutes to prepare a disrupted cell suspension. In the treatment, an ultrasonic disintegrator Model UR200P (product of Tomy Seiko Co., Ltd.) is used.

Preparation of substrate solution

In this step, 120 mg of (±)-cis-7-amino-1-azabicyclo[4,2,0]oct-2-en-8-on-2-carboxylic acid obtained as in Example 10 of U.S. Ser. No. 23,645 and G.O. No. 2911786 and 500 mg of the hydrochloride of D-phenylglycinmethylester are added to 9 ml of 1/30 M potassium phosphate buffer (pH 6.5). Then 5 N-KOH is added in small portions and the mixture is again adjusted to a pH of 6.5 to dissolve the two starting compounds. Finally, deionized water is added to make up 10 ml of solution.

Enzyme reaction

In this step, 10 ml of the disrupted cell suspension is added to 10 ml of the substrate solution and the enzyme reaction is carried out at a temperature of 30° C. for 5 hours. The reaction is monitored by high speed liquid chromatography using TRI ROTAR (product of Nippon Bunko Co., Ltd.) and Prepack column Nucleosil 10C18 (product of Gaskuro Kogyo Co., Ltd.). Elution is carried out with a 7% methanol-0.2 M $KH_2PO_4$ solution. The reaction reaches maximum in 5 hours.

Isolation and purification of the desired compound

After completion of the reaction, the microbial cells are removed from the reaction solution by centrifugation. The supernatant is concentrated under reduced pressure and charged on a column (1.6 cm width, 50 cm height) packed with 100 ml of Diaion HP-10 (product of Mitsubishi Kasei Kogyo Co., Ltd.). After washing with 200 ml of deionized water, elution is carried out with 30% aqueous methanol solution. The eluate is collected in 10 ml fractions. Fraction Nos. 20 to 25, containing the desired compound, are concentrated under reduced pressure to make 5 ml of concentrate. The concentrate is charged on a column (1.6 cm width, 64.5 cm height) packed with 130 ml of Sephadex-LH20 (Pharmacia Fine Chemicals Inc.) and elution is carried out with a mixture of water and methanol (50:50 by volume, the same shall apply hereinafter). The eluate is collected in 5 ml fractions. The desired compound is eluted in the fractions from 60 ml to 80 ml. The fractions are concentrated under reduced pressure to remove methanol and the residue is lyophilized to obtain 81 mg of a white powder having the following properties.

$[\alpha]_D^{22°}$ ($H_2O$, c=0.5): +57.2°.

IR(KBr)$\nu_{max}{}^{cm-1}$: 1760, 1690, 1640.

PMR($D_2O$)$\delta$(ppm): 7.51(5H, s), 6.08(1H, t, J=4.2 Hz), 5.41(1H, d, J=4.9 Hz), 5.19(1H, s), 3.83(1H, octet, J=8.6, 4.9 Hz), 2.28–0.01(4H, m).

The values mentioned above coincide with those of the less polar isomer in Example 6 of U.S. Ser. No. 23,646 and G.O. No. 2911787. Based on this data, the white powder is identified as the desired compound. From the strong antimicrobial activity, the absolute configuration of this compound is assumed to be (6R, 7S).

EXAMPLE 2

Preparation of (+)-7$\beta$-[(R)-2-phenyl-2-aminoacetamido]-4$\alpha$-methyl-1-azabicyclo[4,2,0]oct-2-en-8-on-2-carboxylic acid [referred to as Compound (B) hereinafter]:

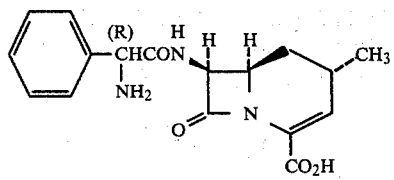

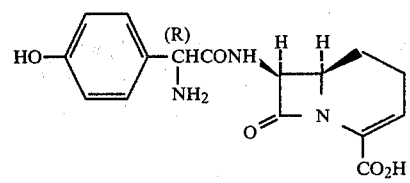

Preparation of cell suspension

A cell suspension is prepared as in Example 1 except that *Xanthomonas citri* IFO 3835, the biological properties of which are described in Bergey's Manual of Determinative Bacteriology VI, P. 156 (1948) is used as the seed strain.

Preparation of substrate solution

In this step, 200 mg of the trifluoroacetate of (±)-cis-7β-amino-4α-methyl-1-azabicyclo [4,2,0] oct-2-en-8-on-2-carboxylic acid obtained as in Example 15 of U.S. Ser. No. 23,645 and G.O. No. 2911786 and 500 mg of the hydrochloride of D-phenylglycinmethylester are added in 9 ml of 1/30 M potassium phosphate buffer (pH 6.5). Then, 5 N-KOH is added in small portions and the mixture is again adjusted to a pH of 6.5 to dissolve the two starting compounds. Finally, deionized water is added to make up 10 ml of a solution.

Enzyme reaction and isolation and purification of the desired compound

In this step, 10 ml of the disrupted cell suspension is added to 10 ml of the substrate solution and the enzyme reaction is carried out at a temperature of 30° C. for 4 hours. The reaction is monitored as in Example 1, and reaches maximum in 4 hours. Then, the same procedure as in Example 1 is repeated to obtain 76 mg of a white powder having the following properties.

$[\alpha]_D^{15°}$ (H$_2$O, c=0.52): +4.23°.

IR(KBr)$\nu_{max}^{cm-1}$: 3420, 1760, 1695, 1633.

PMR(D$_2$O)δ(ppm): 7.51(5H, s), 6.10(1H, d, J=5.1 Hz), 5.19(1H, s), 3.89(1H, m), 2.45(1H, m), 1.44–1.04(2H, m), 1.00(3H, d, J=7.4 Hz).

The values mentioned above coincide with those of the less polar isomer obtained in Example 12 of U.S. Ser. No. 23,646 and G.O. No. 2911787. Based on this data, the white powder is identified as the desired compound. From the strong antimicrobial activity, the absolute configuration of this compound is assumed to be (4S, 6R, 7S).

EXAMPLE 3

Preparation of Compound (A) (Alternative method):

In this example, *Escherichia coli* ATCC 11105, the biological properties of which are described in Bergey's Manual of Determinative Bacteriology VIII P. 295 (1974) is used as the seed strain. The same procedure as in Example 1 is repeated except that the enzyme reaction is carried out for 12 hours to obtain 39 mg of a white powder. The properties of the product coincide well with those of the compound obtained in Example 1.

EXAMPLE 4

Preparation of (+)-7-[(R)-2-p-hydroxyphenyl-2-aminoacetamido]-1-azabicyclo[4,2,0]oct-2-en-8-on-2-carboxylic acid:

Cultivation of microorganism having an ability of optically selective acyltion

The same procedure as in Example 1 is repeated except that *Kluyvera citrophila* ATCC 21285, the biological properties are described in J. General Applied Microbiology 3, 28–31 (1957) is used as the seed strain.

Preparation of cell suspension

After culturing for 24 hours, the cell bodies are recovered from the culture broth by centrifugation and washed twice with 50 ml of 0.9% saline solution. The cells are suspended in a concentration of 40 mg/ml by dry weight in 1/30 M phosphate buffer.

Preparation of substrate solution

In this step, 120 mg of (±)-cis-7-amino-1-azabicyclo[4,2,0]oct-2-en-8-on-2-carboxylic acid obtained as in Example 10 of U.S. Ser. No. 23,645 and G.O. No. 2911786 and 500 mg of the hydrochloride of D-p-hydroxyphenylglycinmethylester are added to 9 ml of 1/30 M potassium phosphate buffer (pH 6.5). Then, 5 N-KOH is added in small portions and the mixture is again adjusted to a pH of 6.5 to dissolve the two starting compounds. Finally, deionized water is added to make up 10 ml of a solution.

Enzyme reaction and isolation and purification of the desired compound

In this step, 10 ml of the cell suspension is added to 10 ml of the substrate solution and the enzyme reaction is carried out at a temperature of 30° C. for 20 hours. The reaction is monitored as in Example 1 and reaches maximum in 20 hours.

The same procedure as in Example 1 is repeated to obtain 65 mg of a white powder having the following properties.

$[\alpha]_D^{20°} = +107.5°$ [c=0.5, 1 M phosphate buffer (pH 7.0)].

IR(KBr)$\nu_{max}^{cm-1}$: 3450, 3290, 3090, 1760, 1700(sh), 1685.

PMR(D$_2$O)δ(ppm): 7.36(2H, d, J=8.8 Hz), 6.95(2H, d, J=8.8 Hz), 6.06(1H, t, J=3.9 Hz), 5.40(1H, d, J=4.6 Hz), 5.12(1H, s), 3.84(1H, m), 2.22(2H, m), 1.62(1H, m), 1.12(1H, m).

Based on this data, the white powder is identified as the desired compound. From the strong antimicrobial activity, the absolute configuration of this compound is assumed to be (6R, 7S).

EXAMPLE 5

Preparation of (+)-7β-[(R)-2-p-hydroxyphenyl-2-aminoacetamido]-4α-methyl-1-azabicyclo[4,2,0]oct-2-en-8-on-2-carboxylic acid:

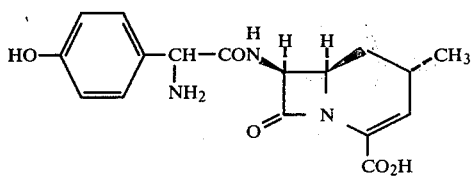

Preparation of cell suspension

A cell suspension is prepared as in Example 4 except that *Xanthomonas citri* IFO 3835 is used as the seed strain.

Preparation of substrate solution

A substrate solution is prepared as in Example 2.

Enzyme reaction and isolation and purification of the desired compound

The same procedures as in Example 1 are repeated using the cell suspension and the substrate solution prepared above to obtain 75 mg of a white powder. The reaction is carried out for 3 hours. Properties of the product are as follows.

$[\alpha]_D^{20°} = +12.8°$ [c=0.5, 1 M phosphate buffer (pH 7.0)].

IR(KBr)$\nu_{max}{}^{cm-1}$: 3420, 3260, 1760, 1685.

PMR(D$_2$O)$\delta$(ppm): 7.35(2H, d, J=8.0 Hz), 6.96(2H, d, J=8.0 Hz), 6.10(1H, d, J=5.1 Hz), 5.45(1H, d, J=4.9 Hz), 5.11(1H, s), 3.92(1H, m), 2.45(1H, m), 1.50–1.08(2H, m), 1.01(3H, d, J=7.1 Hz).

Based on this data, the white powder is identified as the desired compound. From the strong antimicrobial activity, the absolute configuration of this compound is assumed to be (4S, 6R, 7S).

EXAMPLE 6

Preparation of Compound (A) (Alternative method):

In this example, the same procedure as in Example 1 is repeated except that 120 mg of (30)-cis-7-amino-1-azabicyclo [4,2,0] oct-2-en-8-on-2-carboxylic acid obtained in Reference Example 1 is used in place of (±)-cis-7-amino-1-azabicyclo [4,2,0] oct-2-en-8-on-2-carboxylic acid to obtain 160 mg of a white powder. The properties of the product coincide with those of the compound obtained as in Example 1.

EXAMPLE 7

Preparation of Compound (B) (Alternative method):

In this example, the same procedure as in Example 2 is repeated except that 150 mg of (−)-cis-7$\beta$-amino-4$\alpha$-methyl-1-azabicyclo [4,2,0] oct-2-en-8-on-2-carboxylic acid obtained in Reference Example 3 is used in place of the trifluoroacetate (±)-cis-7$\beta$-amino-4$\alpha$-methyl-1-azabicyclo [4,2,0] oct-2-en-8-on-2-carboxylic acid to obtain 150 mg of a white powder. The properties of the product coincide with those of the compound obtained in Example 2.

EXAMPLE 8

In this example, the antibacterial activity of the compounds obtained in Examples 1, 2, 4 and 5 are determined and the results are set forth in Table 1. The compounds obtained in the Examples of U.S. Ser. No. 23,646 and G.O. No. 2911787 and cephalexin are used as controls.

The determinative is made by Heart Infusion Agar Dilution Method (pH 7.2). In Table 1, the numbers of the compound represent the following compounds and the letters A to M represent the following strains.

1. (+) compound obtained in Example 1
2. (±) compound obtained in Example 6 of U.S. Ser. No. 23,646 and G.O. No. 2911787
3. (−) compound obtained in Example 6 of U.S. Ser. No. 23,646 and G.O. No. 2911787
4. (+) compound obtained in Example 2
5. (±) compound obtained in Example 12 of U.S. Ser. No. 23,646 and G.O. No. 2911787
6. (−) compound obtained in Example 12 of U.S. Ser. No. 23,646 and G.O. No. 2911787
7. (+) compound obtained in Example 4
8. (+) compound obtained in Example 47 of U.S. Ser. No. 23,646 and G.O. No. 2911787
9. (+) compound obtained in Example 5
10. (+) compound obtained in Example 44 of U.S. Ser. No. 23,646 and G.O. No. 2911787
11. Cephalexin (control)

A. *Staphylococcus aureus* 209-P
B. *Staphylococcus aureus* Smith
C. *Staphylococcus epidermidis*
D. *Escherichia coli* NIHJC-2
E. *Escherichia coli* Juhl
F. *Klebsiella pneumoniae* 8045
G. *Klebsiella pneumoniae* Y-60
H. *Serratia marcescens* T-26
I. *Serratia marcescens* T-55
J. *Proteus mirabilis* 1287
K. *Proteus vulgaris* 6897
L. *Proteus morganii* KY4298
M. *Proteus rettgeri* KY4289

As will be noted from the Table, the MIC of the (+) compounds obtained in Examples 6 and 12 of G.O. No. 2911787 coincide with MIC of the (+) compounds obtained in Examples 1 and 2.

TABLE 1

| Strain | Compound | | | | | | | | | | |
|---|---|---|---|---|---|---|---|---|---|---|---|
| | 1 | 2 | 3 | 4 | 5 | 6 | 7 | 8 | 9 | 10 | 11 |
| A | 0.4 | 0.4 | — | 0.78 | 0.78 | — | 0.4 | 1.56 | 0.4 | 0.4 | 0.2 |
| B | 6.25 | 12.5 | — | 6.25 | 6.25 | — | 3.12 | 12.5 | 1.56 | 1.56 | 3.12 |
| C | 3.12 | 6.25 | — | 3.12 | 6.25 | — | 1.56 | 6.25 | 0.78 | 1.56 | 3.12 |
| D | 3.12 | 12.5 | 50 | 12.5 | 12.5 | 50 | 3.12 | 12.5 | 6.25 | 6.25 | 12.5 |
| E | 3.12 | 12.5 | 100 | 12.5 | 12.5 | 100 | 6.25 | 12.5 | 6.25 | 6.25 | 12.5 |
| F | 0.78 | 3.12 | 50 | 0.78 | 3.12 | 50 | 0.78 | 3.12 | 3.12 | 12.5 | 3.12 |
| G | 3.12 | 12.5 | 50 | 25 | >100 | 50 | 3.12 | 12.5 | 100 | >100 | 50 |
| H | — | >100 | — | >50 | >100 | — | 100 | — | 50 | 100 | >100 |
| I | 12.5 | 25 | 100 | 25 | >100 | 100 | 6.25 | 50 | 12.5 | 50 | 50 |
| J | 12.5 | 25 | 25 | 25 | 50 | 25 | 50 | 50 | 25 | 50 | 25 |
| K | 50 | 25 | 25 | 25 | 50 | 25 | 100 | — | 100 | >100 | 25 |
| L | 50 | 100 | 50 | 25 | 100 | 50 | 100 | — | 100 | >100 | >100 |

TABLE 1-continued

| Strain | Compound | | | | | | | | | | |
|---|---|---|---|---|---|---|---|---|---|---|---|
| | 1 | 2 | 3 | 4 | 5 | 6 | 7 | 8 | 9 | 10 | 11 |
| M | 12.5 | 50 | 6.25 | 12.5 | >100 | — | 12.5 | 25 | — | — | >100 |

EXAMPLE 9

In this example, Compound (A) is prepared by the following alternative methods.

Cultivation of microorganisms

As the seed strain, the following strains are used.
Aeromonas hydrophila IFO 12634
Achromobacter aceris IFO 3320
Arthrobacter simplex ATCC 15799
Acetobacter aurantius IFO 3245
Acetobacter sp. ATCC 21760
Alcaligenes faecalis ATCC 8750
Escherichia coli ATCC 13281
Xanthomonas physalidicola IFO 13555
Gluconobacter liquefaciens ATCC 14835
Gluconobacter dioxyacetonicus IFO 3271
Comamonas terrigena IFO 12685
Corynebacterium tritici IFO 12164
Sarcina lutea ATCC 9341
Staphylococcus aureus IFO 3060
Spirillum metamorphum IFO 12012
Bacillus megaterium ATCC 14945
Pseudomonas aeruginosa IFO 3451
Flavobacterium sp. ATCC 21429
Brevibacterium cerinum ATCC 15112
Protaminobacter alboflavus IFO 13221
Proteus rettgeri ATCC 9250
Beneckea hyperoptica ATCC 15803
Micrococcus luteus AHU 1427
Mycoplana bullata IFO 13267
Mycoplana dimorpha IFO 13213
Rhodopseudomonas spheroides ATCC 21286

As the medium, an aqueous solution containing 1% meat extract, 1% peptone, 0.3% sodium chloride, 0.5% yeast extract and adjusted at a pH of 7.2 with 5 N-NaOH is used. One loopful of the seed strain is inoculated into 30 ml of the medium in a 300 ml Erlenmeyer flask and culturing is carried out with shaking at a temperature of 30° C. for 24 hours. The cell bodies are then recovered from the culture broth by filtration and washed with 5 ml of 0.9% sodium chloride solution. The cells are again recovered by centrifugation and suspended in a concentration of 40 mg/ml by dry weight in 1/30 M phosphate buffer (pH 6.5).

Preparation of substrate solution

A substrate solution is obtained as in Example 1. That is, 123 mg of (±)-cis-7-amino-1-azabicyclo[4,2,0]oct-2-en-8-on-2-carboxylic acid and 400 mg of the hydrochloride of D-phenylglycinmethylester are added to 15 ml of 1/30 M phosphate buffer (pH 6.5). Then, 5 N-KOH is added in small portions and the mixture is adjusted to a pH of 6.5 to dissolve the two starting compounds. Finally, deionized water is added to make up 20 ml of a solution.

Enzyme reaction

The same procedure as in Example 4 is carried out using 0.5 ml of the cell suspension and 0.5 ml of the substrate solution. The reaction is carried out at a temperature of 30° C. for 24 hours.

Identification of the desired compound

The reaction is monitored by high speed liquid chromatography in the same manner as in Example 1.

As apparent from Table 2, the desired more polar diastereoisomer, i.e. (−)-cis-7-[(R)-2-phenyl-2-aminoacetamido]-1-azabicyclo[4,2,0]oct-2-en-8-on-2-carboxylic acid [Example 6 of U.S. Ser. No. 23,646 and G.O. No. 2911787] is not formed at all and only the desired less polar isomer, i.e. (+)-cis-7-[(R)-2-phenyl-2-aminoacetamido]-1-azabicyclo[4,2,0]oct-2-en-8-on-2-carboxylic acid is formed. The enzyme produced by all strains in Table 2 have an ability for optically selective acylation of cephalosporin analogs.

TABLE 2

| Microorganism | Amount of Compound (A) produced (mg)* |
|---|---|
| Aeromonas hydrophila IFO 12634 | 0.05 |
| Achromobacter aceris IFO 3320 | 0.08 |
| Arthrobacter simplex ATCC 15799 | 0.06 |
| Acetobacter aurantius IFO 3245 | 0.04 |
| Acetobacter sp. ATCC 21760 | 1.02 |
| Alcaligenes faecalis ATCC 8750 | 0.04 |
| Escherichia coli ATCC 13281 | 0.25 |
| Xanthomonas physalidicola IFO 13555 | 0.95 |
| Gluconobacter liquefaciens ATCC 14835 | 0.13 |
| Gluconobacter dioxyacetonicus IFO 3271 | 0.20 |
| Comamonas terrigena IFO 12685 | 0.03 |
| Corynebacterium tritici IFO 12164 | 0.07 |
| Sarcina lutea ATCC 9341 | 0.05 |
| Staphylococcus aureus IFO 3060 | 0.09 |
| Spirillum metamorphum IFO 12012 | 0.18 |
| Bacillus megaterium ATCC 14945 | 0.05 |
| Pseudomonas aeruginosa IFO 3451 | 0.03 |
| Flavobacterium sp. ATCC 21429 | 0.04 |
| Brevibacterium cerinum ATCC 15112 | 0.20 |
| Protaminobacter alboflavus IFO 13221 | 1.21 |
| Proteus rettgeri ATCC 9250 | 0.09 |
| Beneckea hyperoptica ATCC 15803 | 0.68 |
| Micrococcus luteus AHU 1427 | 0.22 |
| Mycoplana bullata IFO 13267 | 0.55 |
| Mycoplana dimorpha IFO 13213 | 0.98 |
| Rhodopseudomonas spheroides ATCC 21286 | 0.11 |

*2.66 mg of the compound should be produced in a yield of 100%.

EXAMPLE 10

Preparation of Compound (A) (Alternative method):

In this Example, Clostridium acetobutylicum ATCC 824 is inoculated in 100 ml of Potato Dextrose Broth (product of DIFCO Lab.). The fermentor is sealed after the air is substituted with sterilized nitrogen and culturing is carried out at a temperature of 30° C. for 48 hours. The cell bodies are then recovered and washed with physiological saline solution. The cells are suspended in 2 ml of 1/30 M potassium phosphate buffer (pH 6.5), and the same reaction as in Example 9 is repeated to obtain 0.12 mg of Compound (A).

REFERENCE EXAMPLE 1

Preparation of (+)-cis-7-amino-1-azabicyclo[4,2,0]oct-2-en-8-on-2-carboxylic acid [referred to as Compound (C) hereinafter].

Cultivation of a microorganism having an ability of optically selective deacylation In this step, *Kluyvera citrophila* ATCC 21285, the biological properties of which are described in J. General Applied Microbiology 3, 28–31 (1957) is used as the seed strain. As the seed medium, an aqueous solution containing 1% polypeptone, 1% yeast extract, 0.5% meat extract, 0.5% sodium glutamate and 0.25% sodium chloride and adjusted to a pH of 7.0 with 5 N-NaOH is used. One loopful of the seed strain is inoculated into 10 ml of the seed medium in a 50 ml large test tube and culturing is carried out at a temperature of 30° C. for 24 hours. The entire seed broth is then inoculated into 300 ml of a culture medium of the same composition as the seed medium in a 2 L. Erlenmeyer flask and culturing is carried out at a temperature of 30° C. with shaking.

Preparation of disrupted cell suspension

After culturing for 24 hours, the culture broth is subjected to centrifugation to obtain the cell bodies. The cells are washed twice with 50 ml of 0.9% saline solution and suspended in a concentration of 40 mg/ml by dry weight in 1/30 M phosphate buffer solution. Then, 10 ml of the cell suspension is put in a 50 ml large test tube and subjected to ultrasonic disintegration at 200 W for 2 minutes to obtain a disrupted cell suspension. In the treatment, ultrasonic disintegrator Model UP200P (product of Tomy Seiko Co., Ltd.) is used.

Preparation of substrate solution

In this step, 200 mg of (±)-cis-7-phenylacetamido-1-azabicyclo[4,2,0]oct-2-en-8-on-2-carboxylic acid obtained as in Example 22 of U.S. Ser. No. 23,646 and G.O. No. 2911787 is added to 9 ml of 1/30 M phosphate buffer (pH 6.5). Since the compound is not dissolved, 2 N-NaOH is added in a small portion and the mixture is again adjusted to a pH of 6.5 to dissolve the compound. Finally, deionized water is added to make 10 ml of a solution.

Enzyme reaction

In this step, 10 ml of the disrupted cell suspension mentioned above is added to 10 ml of the substrate solution and enzyme reaction is carried out at a temperature of 30° C. for 80 minutes. The time course of the reaction is illustrated in Table 3.

TABLE 3

| Reaction period (minutes) | The amount of Compound (C) produced (mg/ml) | Yield (Mol ratio, %) |
|---|---|---|
| 10 | 2.0 | 33 |
| 20 | 2.6 | 43 |
| 40 | 2.9 | 48 |
| 60 | 3.0 | 50 |
| 80 | 3.0 | 50 |

As apparent from Table 3, the reaction and yield became stationary since the conversion ratio of the mixture of the optically active isomers reaches 50% (mol ratio).

Isolation and purification of the desired compound

After completion of the reaction, the microbial cells are removed by centrifugation from the reaction solution. The supernatant is adjusted to a pH of 3.0 with 2 N-hydrochloric acid and charged on a column (2.6 cm width, 51 cm height) packed with 270 ml of Diaion HP-10 (product of Mitsubishi Kasei Kogyo Co., Ltd.). Elution is carried out with deionized water and the eluate is collected in 5 ml fractions. The desired compound is eluted in the fractions from 280 ml to 315 ml. The fractions are concentrated under reduced pressure, lyophilized and dissolved in a small amount of a mixture of water and methanol (50:50 by volume, as is used hereinafter). The solution is then charged on a column (1.6 cm width, 64.5 cm height) packed with 130 ml of Sephadex LH-20 (Pharmacia Fine Chemicals Inc.). Elution is carried out with a mixture of water and methanol (50:50). The eluate is collected in 5 ml fractions. Fractions from 65 ml to 85 ml are combined and concentrated under reduced pressure to remove methanol. Then, the residue is lyophilized to obtain 48 mg of a white powder having the following properties.

IR(KBr)$\nu_{max}^{cm-1}$: 1800, 1790, 1775, 1640, 1620.

NMR(100 M D$_2$O-DSS)δ(ppm): 6.46(1H, dd, J=3.5, 4.7 Hz), 4.88(1H, d, J=5.2 Hz), 4.06(1H, m), 2.5–1.5(4H, m).

It is determined that the compound has one mole of hydrochloric acid and water. The properties of the compound coincide well with those of the corresponding dl-compound. The value of optical rotation is $[\alpha]_D^{15°} = +48°$ [c=0.5, in 1 M phosphate buffer solution (pH 7.0)] which coincides well with the value in Reference Example 2 below, $[\alpha]_D^{15°} = 48.5°$ [c=0.5, in 1 M phosphate buffer solution (pH 7.0)].

The compound shows a ninhydrin positive single spot at an Rf value of 0.22 on silica gel thin layer chromatography [thin layer plate Merck Art 5721 (product of E. Merck & Co.), solvent for development, isopropanol:acetic acid:water=4:1:1]. The Rf value coincides with that of the optically inactive dl-compound.

REFERENCE EXAMPLE 2

Preparation of (+)-cis-7-amino-1-azabicyclo[4,2,0]oct-2-en-8-on-2-carboxylic acid (Alternative method).

Preparation of disrupted cell suspension

The same procedure as in Example 1 is repeated.

Preparation of a substrate solution

In this step, 100 mg of (+)-cis-7-[(R)-2-phenyl-2-aminoacetamido]-1-azabicyclo[4,2,0]oct-2-en-8-on-2-carboxylic acid obtained as in Example 6 of U.S. Ser. No. 23,646 and G.O. No. 2911787 is dissolved in 5 ml of 1/30 M phosphate buffer solution (pH 6.5).

Enzyme reaction

In this step, 5 ml of the disrupted cell suspension mentioned above is added to 5 ml of the substrate solution and enzyme reaction is carried out of 30° C. for 24 hours.

Isolation and purification

In this step, 46 mg of a white powder is obtained by a similar method as in Reference Example 1. The properties of the compound coincide well with those of the compound obtained in Reference Example 1.

$[\alpha]_D^{15°} = 48.5°$ [c=0.5, in 1 M phosphate buffer solution (pH 7.0)].

REFERENCE EXAMPLE 3

Preparation of (−)-cis-7β-amino-4α-methyl-1-azabicyclo[4,2,0]oct-2-en-8-on-2-carboxylic acid.

Preparation of disrupted cell suspension

A similar procedure as in Reference Example 1 is repeated.

Preparation of substrate solution

A similar procedure as in Reference Example 1 is repeated except that (±)-cis-7β-phenylacetamido-4α-methyl-1-azabicyclo[4,2,0]oct-2-en-8-on-2-carboxylic acid obtained as in Example 23 of U.S. Ser. No. 23,646 and G.O. 2911787 is used.

Enzyme reaction

A similar procedure as in Reference Example 1 is repeated except that the disrupted cell suspension and the substrate solution obtained in the foregoing steps are used. The reaction ratio becomes stationary in one hour. The reaction is continued, however, for 120 minutes. The yield is 50% (mol ratio) of the mixture of optically active compounds.

Isolation and purification of the desired compound

In this step, a procedure similar to that used in Reference Example 1 is used. After completion of the reaction, the microbial cells are removed by centrifugation from the reaction solution. The supernatant is charged on a column (2.5 cm width, 46 cm height) packed with 220 ml of Diaion HP-10. Elution is carried out with deionized water and the eluate is collected in 5 ml of fractions. The desired compound is eluted in the fractions from 200 ml to 270 ml. The fractions are concentrated under reduced pressure, lyophilized, and dissolved in a small amount of water and methanol (50:50). The solution is charged on a column (1.6 cm width, 64.5 cm height) packed with 130 ml of Sephadex LH-20 and elution is carried out with a mixture of water and methanol (50:50). The eluate is collected in 5 ml of fractions. The fractions from 65 ml to 80 ml are combined and concentrated to remove methanol. Then, the residue is lyophilized to obtain 30.5 mg of a white powder having the following properties.

IR(KBr)$\nu_{max}^{cm-1}$: 1800, 1770(sh), 1760(sh), 1740, 1680, 1630.

NMR(100 M D$_2$O-DSS)δ(ppm): 6.16(1H, d, J=5.1 Hz), 4.52(1H, d, J=4.9 Hz), 3.86(1H, m), 2.64(1H, m), 1.9–1.4(2H, m), 1.10(3H, d, J=7.3 Hz).

It is determined that the compound is a potassium salt having 2 moles of water. The properties above coincide well with those of the corresponding dl compound. The compound also shows a ninhydrin positive single spot at an Rf of 0.33 on a silica gel thin layer chromatography (the same silica gel as in Reference Example 1 is used). The Rf value coincides with that of the optically inactive dl-compound.

Optical rotation $[\alpha]_D^{15°} = -30°$ (c=0.5, in 1 M phosphate buffer solution). The value coincides well with that in Reference Example 4, $[\alpha]_D^{15°} = -30.8°$ [c=0.5, in 1 M phosphate buffer solution (pH 7.0)].

REFERENCE EXAMPLE 4

Preparation of (−)-cis-7β-amino-4α-methyl-1-azabicyclo[4,2,0]oct-2-en-8-on-2-carboxylic acid (Alternative method).

Preparation of disrupted cell suspension

A procedure as in Reference Example 3 is repeated.

Preparation of substrate solution

In this step, 100 mg of (+)-cis-7β-[(R)-2-phenyl-2-aminoacetamido]-4α-methyl-1-azabicyclo[4,2,0]oct-2-en-8-on-2-carboxylic acid obtained as in Example 12 of U.S. Ser. No. 23,646 and G.O. No. 2911787 is dissolved in 5 ml of 1/30 M phosphate buffer solution (pH 6.5).

Enzyme reaction

As in Reference Example 1, 5 ml of the disrupted cell suspension described above is added to 5 ml of the substrate solution and enzyme reaction is carried out at a temperature of 30° C. for 24 hours.

Isolation and purification of the desired product

A similar procedure as in Reference Example 3 is repeated to obtain 55 mg of a white powder. Properties of the compound coincide well with those in Reference Example 3.

Optical $[\alpha]_D^{15°} = -30.8°$ [c=0.5, in 1 M phosphate buffer solution (pH 7.0)].

What is claimed is:

1. A process for producing optically active compounds of the formula

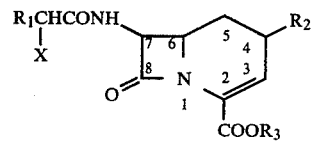

wherein R$_1$ represents a substituted or unsubstituted saturated or unsaturated six-membered carbocyclic or five-membered heterocyclic group, R$_2$ represents a hydrogen or a lower alkyl group, R$_3$ represents a hydrogen or a protective group of carboxylic acid, X represents a hydrogen, a lower alkyl group, a hydroxy group, a carboxy group or an amino group, and the hydrogens at the 6- and 7-positions have cis configuration and salts thereof which comprises reacting an α,α-disubstituted carboxylic acid represented by the formula

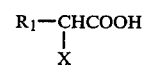

wherein R$_1$ and X have the same significance as defined above or a reactive derivative thereof and a compound represented by the formula

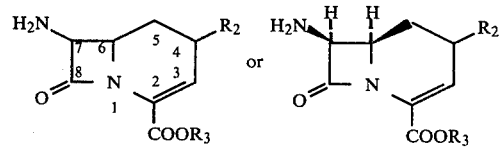

wherein R$_2$ and R$_3$ have the same significance as defined above in the presence of an enzyme capable of catalyzing optically selective acylation and derived from a microorganism belonging to the genus Pseudomonas, Xanthomonas, Escherichia, Aeromonas, Achromobacter, Arthrobacter, Acetobacter, Alcaligenes, Kluyvera, Gluconobacter, Clostridium, Comamonas, Corynebacterium, Sarcina, Staphylococcus, Spirillum, Bacillus, Flavobacterium, Brevibacterium, Protaminobacter, Beneckea, Micrococcus, Proteus, Mycoplana or Rhodopseudomonas and thereafter isolating said optically active compound from the reaction mixture.

2. A process according to claim 1 wherein said microorganism belongs to the species *Pseudomonas melanogenum, Xanthomonas citri, Escherichia coli, Kluyvera citrophila, Aeromonas hydrophila, Achromobacter aceris, Arthrobacter simplex, Acetobacter aurantius, Alcaligenes faecalis, Xanthomonas physalidicola, Gluconobacter liquefaciens, Gluconobacter dioxyacetonicus, Comamonas terrigena, Corynebacterium tritici, Sarcina lutea, Staphylococcus aureus, Spirillum metamorphum, Bacillus megaterium, Pseudomonas aeruginosa, Brevibacterium cerinum, Protaminobacter alboflavus, Proteus rettgeri, Beneckea hyperoptica, Micrococcus luteus, Mycoplana bullata, Mycoplana dimolpha, Rhodopseudomonas spheroides, Clostridium acetobutylicum,* Acetobacter sp. ATCC 21760 or Flavobacterium sp. ATCC 21429.

3. A process according to claim 1 wherein said enzyme is provided to said reaction in the form of a purified enzyme solution, cell bodies recovered from a culture broth, a cell suspension, a disrupted cell suspension, a cell free extract or a culture liquor of the microorganism.

4. A process according to claim 1 wherein said reaction is carried out at a temperature of from 0° to 50° C. and at a pH of 5 to 8 for 30 minutes to 24 hours.

5. A process according to claim 1 wherein the concentration of said enzyme is equivalent in activity to 1 to 50 mg by dry weight of microbial cells per ml of reaction solution.

* * * * *

UNITED STATES PATENT AND TRADEMARK OFFICE
CERTIFICATE OF CORRECTION

PATENT NO. : 4,332,896
DATED : June 1, 1982
INVENTOR(S) : YUKIO HASHIMOTO, et al.

It is certified that error appears in the above-identified patent and that said Letters Patent is hereby corrected as shown below:

Column 3, lines 32 -39, in the formula designated as "(III-1)", delete "  ".

Column 11, line 41, "(30)" should be -- (+) --.

Column 16, line 55, "of" should be -- at --.

Column 19, claim 2, line 16, "dimolpha" should be -- dimorpha --.

Signed and Sealed this

Seventh Day of September 1982

[SEAL]

Attest:

GERALD J. MOSSINGHOFF

Attesting Officer    Commissioner of Patents and Trademarks